United States Patent [19]

Pardikes

[11] Patent Number: 5,403,552
[45] Date of Patent: Apr. 4, 1995

[54] MODULE FOR AUTOMATICALLY CONTROLLING A POLYMER PROCESSING SYSTEM

[76] Inventor: Dennis Pardikes, 12811 S. 82nd St., Palos Park, Ill. 60464

[21] Appl. No.: 12,412

[22] Filed: Feb. 16, 1993

Related U.S. Application Data

[63] Continuation-in-part of Ser. No. 843,409, Feb. 28, 1992, abandoned, Ser. No. 871,066, Jun. 5, 1986, abandoned, Ser. No. 139,075, Dec. 28, 1987, abandoned, Ser. No. 352,689, May 10, 1989, abandoned, and Ser. No. 504,910, Jun. 20, 1990, Pat. No. 5,051,940.

[51] Int. Cl.$^6$ .............................................. G01N 21/00
[52] U.S. Cl. ....................................... 422/62; 422/111
[58] Field of Search .................................... 422/62, 111

[56] References Cited

U.S. PATENT DOCUMENTS

| | | | |
|---|---|---|---|
| 3,574,553 | 1/1968 | Weitz et al. | 422/62 |
| 4,155,774 | 5/1979 | Randolph | 422/111 |
| 4,621,063 | 11/1986 | Wyatt et al. | 422/67 |

Primary Examiner—Lyle A. Alexander
Attorney, Agent, or Firm—Laff, Whitesel, Conte & Saret

[57] ABSTRACT

A controller for a polymer processing system operates by emitting a controlled amplitude and frequency of coherent light (laser) energy which is scattered and absorbed by the monitored polymer dispersed throughout an instantaneous aqueous sample of a monitored material flowing continuously through a cross section of a sample chamber. The source of light energy is located an adjustable distance from one side of the sample chamber. An optical receiver (a photoresistor with a selectable filter) measures the amount of light received on the other side of the sample chamber. An output signal of the receiver may be converted into a usable process signal which is then transmitted as an input control signal to a process controller (microprocessor or microcomputer). The process controller output and display can be configured to control and read in any suitable manner. When the monitored system has feedback, the receiver output may be applied through a feedback control loop. Active polymer solids or any other relevant engineering unit or scale, such as percent concentration, may be displayed. The receiver output signal may also operate any suitable controls of any other suitable system, such as in a dairy industry application.

20 Claims, 2 Drawing Sheets

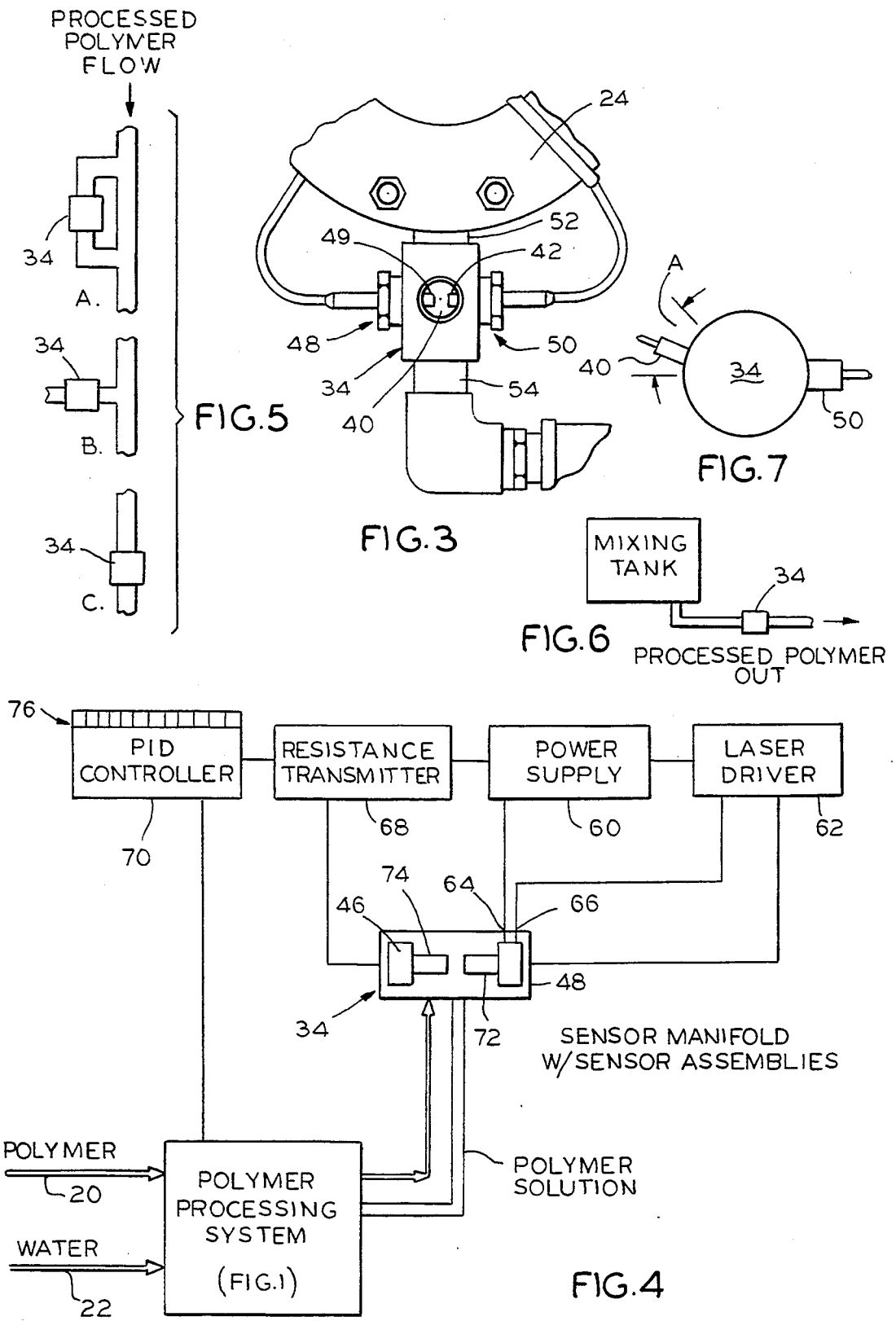

MODULE FOR AUTOMATICALLY CONTROLLING A POLYMER PROCESSING SYSTEM

This is a continuation-in-part of Ser. No. 07/843,409, filed Feb. 28, 1992, (now abandoned); Ser. No. 06/871,066, filed Jun. 5, 1986, now abandoned; Ser. No. 07/139,075, filed Dec. 28, 1987, now abandoned; Ser. No. 07/352,689, filed May 10, 1989, (now abandoned); Ser. No. 07/504,910, filed Jun. 20, 1990; now U.S. Pat. No. 5,051,940.

This invention relates, in general, to optical analyzers for liquids and liquids containing hydrocarbon and polymer gel constituents, and more particularly to analyzer modules which are capable of automatically monitoring and controlling aqueous polymer compositions with hydrocarbon concentrations of polymer or polymer gel constituents produced through a polymer processing and delivery system.

For convenience of expression, the word "polymer" is used herein to cover all suitable systems without regard as to what they can do or are actually processing. In greater detail, while the inventive analyzer may be used in many fields, to test and analyze many products, it is particularly useful for analyzing polymers. These polymers include—but are not necessarily limited to—synthetically and naturally occurring polymers used in charge neutralization, coagulation, flocculation, and emulsification applications. Another particularly useful application of the invention is in the dairy industry where butter fat is first removed and then back blended into milk. These and similar polymers are blended, activated or otherwise processed in many different system, a few of which are shown in the above-identified patents, patent applications, and similar disclosures.

As a general description, a polymer can be defined as a chemical compound made up of repeating structural units which are comprised mainly of carbon and hydrogen. The structural units, or monomers, are linked together to form long chains in a process called "polymerization". If the monomers are positively charged, the polymer is referred to as "cationic" because it migrates to a cathode. A typical cationic polymer contains positively charged nitrogen ions on some or all of its repeating units. When the polymer is comprised of negatively charged units, it is termed "anionic", again because it migrates to an anode. An anionic polymer, for example, may get its charge from negatively charged oxygen ions. If the net charge on the polymer is zero, it is described as "nonionic". A nonionic polymer can result from either an equal combination of negative and positive units or from an absence of charged groups along its chain.

If a polymer is made up of only one type of repeating unit, or monomer, it is a "homopolymer". If two types of monomer uniformly alternate along a polymer backbone, it is a "copolymer". The number and type of repeating units comprising a polymer molecule determine its molecular weight. Since many monomer units are required to make up a polymer, these weights may be very high, ranging from ten thousand to more than ten million.

"Gels" are colloidal suspensions in which the dispersed, natural or synthetic polymer phase, has combined with the continuous, aqueous, phase to produce a semi-solid material. Gels are also fluid-like colloidal systems having long-chain, nitrogen-containing, macromolecules in a semi-solid form. "Emulsions" are dispersions of high-solids synthetic polymer gels in hydrocarbon oil. All solid synthetic polyelectrolytes result from differences in a processing of a polymer prepared in aqueous solutions, or in an aqueous phase of suspension. The synthesis results in a rigid, tough, rubbery gel. Processing the tacky gel particles, with heat, produces the "dry" or "powder" solid polyelectrolyte product.

In general, an activation of liquid polymers is a compound/complex continuum of multistage organic chemical reactions. Depending on the characteristic of the polymer, the activation may require one or more distinctive and successive stages.

Liquid emulsion polymer or micro emulsion polymer (whether 25% to 40% active inverse-emulsions, or 50% to 70% active dispersions) require two distinct processing steps to completely activate the aqueous polymer solution product. These two steps are inversion and aging, similar to the systems described in the above-identified patent applications. In the inversion phase, polymer processing systems "break" the emulsion by subjecting the mixture of high-active-solids polymer gel particles to high-energy, high shear, pressure and mixing gradient forces which instantaneously disperse the continuous oil phase and release the discontinuous polymer gel particles, thereby freeing the polymer to dissolve in the dilution water through hydration and molecular diffusion. In the aging step, the liberated polymer particles are allowed to hydrate and diffuse, in-line or in specially designed holding tanks.

Solution polymers (whether 2% to 7% high molecular weight active or 5% to 60% low molecular weight active) may require only one processing step. The high turbulence high energy blending associated with the above-mentioned systems are usually enough to provide an active in-line homogenous aqueous polymer solution.

The ideal polymer processing system should perform at least two functions. (1) It should provide an active and homogenous polymer solution and; (2) should maintain a desirable relationship (ratio) between the volume of solvent or diluent (water) and the volume of polymer (solute). Additionally this relationship or ratio should be adjustable over a usable range. The polymer particles and associated constituents in a ratio with the aqueous diluent, form a polymer composition which is the "concentration" of the solution.

The concentration of the polymer solution is an important aspect. Too great a concentration causes a polymer overdose result with a negative effect. Too small a concentration causes a polymer underdose that has a similar negative effect. Therefore, it is extremely important to maintain the proper dosage range when applying a polymer. Controlling the concentration of the polymer is one important variable.

Another aspect of maintaining proper polymer concentration involves the "breaking" or inversion of an emulsion type polymer. Too great a dilution results in a low concentration which might wash away necessary inverting agents called "activators" or "surfactants" which are useful in emulsifying hydrocarbon carriers. At the start of the polymer processing procedure, the concentration of a polymer solution is established by setting the diluent flow rate and the polymer flow rate at a desired ratio. For example, a 1% solution concentration setpoint is established by rationing 1 part of polymer to 100 parts of diluent. (Polymer to Water 1:100)

An ideal analyzer should continuously sense the polymer particles and associated constituents freed in the aqueous medium and should provide pertinent concentration information. If the sensed concentration begins to depart from the desired setpoint, signals from the analyzer should be fed back to adjust the polymer processing system. While the system is being so adjusted, the analyzer should monitor to avoid over correction. When the polymer mixture approaches the desired concentration setpoint, the process should be stabilized and then maintained there.

Other fluids, liquids, gels and the like have similar problems which may be addressed by the invention. For example, milk and milk products may also be monitored continuously by the invention. Thus, for example, during processing, milk is first separated from its butter fat and then the butter fat is blended back into the milk at the appropriate concentrations. This process may be monitored or controlled by the invention.

In the inventive system, a sensor manifold assembly or sample block or sample chamber (hereinafter "sample chamber") may be either a stand alone component or a part of another assembly, such as a premix manifold. The sample chamber can be installed to accept either a full process flow or a partial process or a bypass flow. These alternatives give great flexibility as, for example, when adding the inventive module for automatically controlling polymer processing to an existing system while retrofitting an installation.

In one instance the sample chamber may be placed downstream of the polymer processing system at a cascaded location after the primary solution has been blended or inverted, etc. and where there may be further dilution by way of secondary or tertiary dilutions. Also, by way of another example, the module for automatically controlling the polymer processing system can be used in the well known cascade control fashion by monitoring the polymer solution as it exits in a holding vessel or aging tank in order to provide a consistence of polymer concentration which heretofore has been unheard of. This is particularly useful in processes like paper making where the polymer is critical to the wet end chemistry of the paper machines.

Accordingly, an object of the invention is to provide new and novel concentration analyzers for many types of liquids. Here, an object is to provide a continuous sensing of the concentration of a polymer or other liquid, semi-liquid, gel or the like. In this connection, an object is to provide an analyzer for a polymer processing system where the solution concentration is monitored and maintained to a desired setpoint.

Another object of the invention is to provide a production system which may be monitored and adjusted continuously. Here, an object is to feed back signals to adjust the system in real time and as required.

In keeping with an aspect of the invention, these and other objects are accomplished by the inventive controller which operates by emitting a controlled amplitude and frequency of coherent light (laser) energy which is scattered and absorbed by the monitored material dispersed throughout an instantaneous aqueous sample of a monitored material flowing continuously through a cross section of a sample chamber. The source of light energy is located an adjustable distance from one side of the sample chamber. An optical receiver (a photoresistor with a selectable filter) measures the amount of light received on the other side of the sample chamber. An output signal of the receiver may be converted into a usable process signal. This signal is then transmitted as an input control signal to a process controller (microprocessor or microcomputer). The process controller display can be configured to read in any suitable terms, such as percent concentration, active polymer solids or any other relevant engineering unit or scale. Of course, the receiver output signal may also be input to any suitable controls of any other suitable system, such as in a dairy industry application.

When the monitored system has feedback, the receiver output may be applied through a feedback control loop so that the process controller may be programmed to proportionally monitor and adjust a processing system such as a polyelectrolyte concentration by automatically controlling the polymer processing and delivery system itself.

BRIEF DESCRIPTION OF THE DRAWINGS

A preferred embodiment of the invention is shown in the attached drawing, wherein:

FIG. 3 pictorially shows how the inventive sensor and sample chamber is connected into a polymer processing system, such as that shown in FIG. 1;

FIG. 4 is a block diagram of the inventive system;

FIG. 5 schematically shows alternative ways of connecting the inventive module into a polymer flow system;

FIG. 6 schematically shows a cascade coupling of the inventive module; and

FIG. 7 graphically illustrates how the angular displacement between a laser light source and a detector may be varied.

Figure 1:
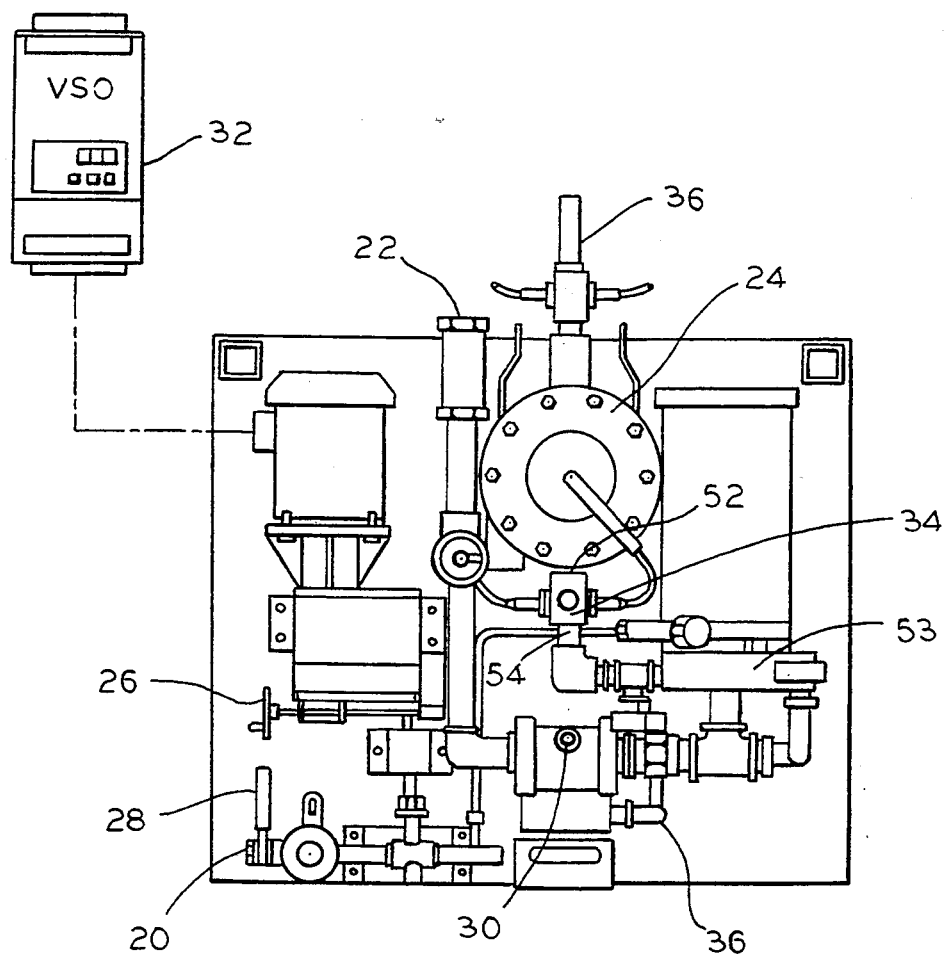
FIG. 1 is a pictorial representation of the mechanical aspects of a system incorporating the invention.

Broadly, a polymer processing system (FIG. 1) has polymer and water intake ports 20, 22, respectively. The polymer and water are mixed in any suitable and known way and then fed through a mixing pressure regulator 24. Various mechanical control handles 26, 28, 30 may be manually adjusted as may be required. These adjustments may be purely mechanical (as opening or closing valves); or, they may be settings of adjustments on electrical controls/actuators.

On control panel 32, various electrical switches or the like may be used to program the system. As here shown, by way of example only, the panel provides a variable speed control. Almost any kind of adjustable device may be accommodated. The inventive sensor sample chamber 34 is here shown, by way of example at the inlet port of the mixing pressure regulator 24 to continuously monitor the solids content of the fluid flowing to the mixing pressure regulator 24. Alternative locations 36, 36 might place the inventive controller/sensor at the output of the system while another location might be on the recycle leg of the polymer mixing loop. The controller/sensor may also be located at any other suitable location in the system.

FIG. 4 shows a block diagram of the electronic controls for the inventive system. The electronic modules depicted in FIG. 4 are located in the main control panel 32 of the system described in FIG. 1. Most of the polymer processing system of FIG. 1 is generally shown in the lower left-hand corner of FIG. 4.

Three elements form the essence of the automatic polymer solution controller system:

a sample chamber, sensor manifold assembly or sample block;

an electronic module; and a process controller.

The sample chamber or sensor manifold assembly 34 (FIG. 2) has a flow chamber 40, in a housing with a transparent viewing port 42, a selective light filter 44, a cadmium sulfide (CdS) photoresistor 46, and a coherent light source (semiconductor laser) emitter 49. The assembly of FIG. 2 has threaded ports which accept diode assembly 48, and resistor lens detector assembly 50.

The laser diode assembly 48 incorporates a semiconductor diode 49, heat sink, lens, static shielding and pin connector housed in a cylindrical threaded body designed for ease of removal from the sample cell. One exemplary laser diode 49 produces light which has a visible light wave length of p=670 nm. Depending on the type of laser used, wavelengths can vary from approximately 300 nm through infrared (>700 nm). In one example, a laser diode with a wavelength of 780 nm may be used in conjunction with a photodiode detector (i.e., a silicon photocell) to take full advantage of polymer compositions that respond favorably to the infrared spectrum. In another example, an ion laser operating at 514 nm may be used for polymer compositions which respond favorably to this wavelength. For both examples, the appropriate lasers would be fitted for use in the module for automatically controlling the polymer system.

The laser light is by far the most efficient way of reading through the polymer solution. However, at the margin of utility and for some polymer solutions, white light may be used instead of the laser light. Therefore, for the convenience of expression, the term "coherent" light is to be construed as any light suitable for a particular polymer solution.

The sample chamber (FIG. 2) may be installed to use either a bypass (FIG. 5A), a partial flow (FIG. 5B) or a full and unrestricted solution flow (FIG. 5C), depending on its relative location in and the nature of the polymer processing system (FIG. 1). FIG. 6 shows the inventive module at a cascaded location downstream of a mixing tank. The output in any of the connections of FIGS. 5 or 6 may be either part of a feedback loop or the output of the system. The flow of a polymer solution through sample chamber 34 (FIG. 2) has to be fast enough to respond to process changes and slow enough so as not to cause an undue turbulence and thus to prevent an efficacious reading.

FIG. 3 shows one example of a connection of the sample chamber assembly into the polymer processing system. In greater detail, a pipe 54 leads from a polymer mixing chamber 53 (FIG. 1) into the sample chamber housing 34 and pipe 52 leads from the housing 34 to the pressure regulator 24 so that the polymer solution flows through the sensor chamber housing 34 during normal processing. The inside diameter of the flow chamber 34 can range from 0.302" to more than 12.0" and flows can range from 0.25 gpm to 5000 gpm. Typically, a sample cell will be designed for a flow velocity of 1 to 10/ft sec. However, a range of 0.3 to 25.0 ft/sec, or more, is possible depending on the rheology of the fluids.

During the flow, a light from laser source 49 (FIG. 2) shines coherent light through the solution in chamber 40 toward the receiver assembly 50. The characteristics of the solution flowing through housing 34 are detected by the differences in the readings taken at the receiver assembly 50.

The sample chamber 34 is designed for a direct opposing scan of the light emitter and detector which seems to be the most efficient arrangement for most polymer solutions. However, there are cases where an off axis scanning is preferred. Basically, the light emitter diode 49 and detector 46 may be set at any suitable angle with respect to each other. This setting tends to emphasize a certain type of particle reflection which is not typically enhanced in direct opposition scanning. The angle of particle reflection A (FIG. 7) may be in the range from 0° to 60°; however, sometimes greater angles may be used if testing warrants it.

In many cases, the level of partical hydration of certain polymers with respect to efficiencies of invention and on blending, aging, etc., may lend itself to angles greater than 60°. Where this is the case, the lenses can be set at 70°, 90°, 120°, 180° or any angle in between. In this arrangement, the optical output of the emitter cell could be increased to compensate for the more radical off axis lense angles.

The automatic polymer solution controller electronic module (FIG. 4) integrates several functions into a single unit. The first function of the module is to provide an adjustable power supply 60 to power a semiconductor laser diode driver 62 and resistance transmitter 68. A special feature is included to protect the semiconductor laser in that power from the power supply 60 is routed to an external connection 64 on the sensor housing 34. A lead from another external connection 66 is returned to the laser light emitting diode 62.

In this inventive example, the semiconductor laser diode 49 (FIG. 2) is powered by a driver circuit rated to deliver up to 150 mA of power. An on board potentiometer enables this driver to be adjusted to the desired output power. The driver can either provide a constant light or optical output via a pin diode feedback or provide a constant current source for the laser diode. This is a selectable feature. The optical feedback loop is designed to maintain a constant light output which is independent of temperature variations at the diode. The feedback loop remedies this temperature caused problem by compensating the amount of drive current delivered to the diode so that the driver current is automatically adjusted upwardly to maintain the same light output level.

Through the use of a plug 69 (FIG. 2) on the diode lens assembly, the connection is made to diode 49 before the diode drive board connection is made. This important feature protects the diode 49 from destructive voltage spikes if the diode connector should be removed while it is receiving power. Additionally, the power supply lead pins on the printed circuit board holding the module of FIG. 4 are mechanically shortened to prevent supply problems caused by spikes if the module is removed or replaced while the processing unit is powered.

The delivery of power to the diode automatically shuts down within milliseconds after the detection of a destructive voltage spike. This feature is built into a laser driver circuit. This is particularly useful when attempting to disconnect or reconnect a diode with the power on. This circuit enhancement both prevents the diode from failing due to a sudden spike, and eliminates the need for special connectors designed to prevent this. This circuit also prevents a user from removing the light emitting diode from the sample chamber while the laser is operating. This is also an important consideration in meeting certain classes of regulating compliance codes.

The module for automatically controlling the polymer solution also includes a resistance transmitter signal conditioning device 68 (FIG. 4) which has separate zero and span settings. The resistance transmitter 68 accepts a resistance signal from the receiving sensor 46 and converts it into a proportional analog output.

Because semiconductor lasers are sensitive to heat from many sources, one has to be particularly careful when monitoring processes that are at a temperature which is higher than ambient temperatures. When running a high temperature solution (above 50° C.) through the sample chamber 34, remoting the emitter and detector cells prevents conductive heat damage to the diode. In the inventive system, fiber optic cables may be fitted to adapter lens housings at the sample chamber and then routed into another enclosure (i.e., control panel) where the emitter and detector are placed away from the heat source. The fiber optic cables are then terminated at ends of the emitter and detector assemblies.

The losses experienced through fiber optic transmission inefficiencies are compensated by increasing the optical output of the laser. Most laser diodes are operated at or above their threshold current values. This is often 70% to 90% of their maximum current value. Thus, for a diode with a maximum operating current value of 100 mA, the threshold current might reasonably reside somewhere around 80 mA. The threshold current is defined as the point in the radiant power output curve where the diode exhibits the special laser light qualities. For most applications, this is where the inventive system seeks to operate.

The process controller 70 is a standard commercially available electronic PID controller (Manufacturer LFE Model PUP). This controller receives the output from the resistance transmitter 68 and displays it at 76 as a process value. The output from the PID controller is then used to control the speed (in this example) of a neat variable speed drive for a polymer injection pump (FIG. 1). Hence, there is a feedback control loop from PID controller 70 to the polymer processing system (FIG. 1), sample chamber 34, resistance transmitter 68, and back to controller 70, which continuously adjusts the polymer processing system.

Figure 2:
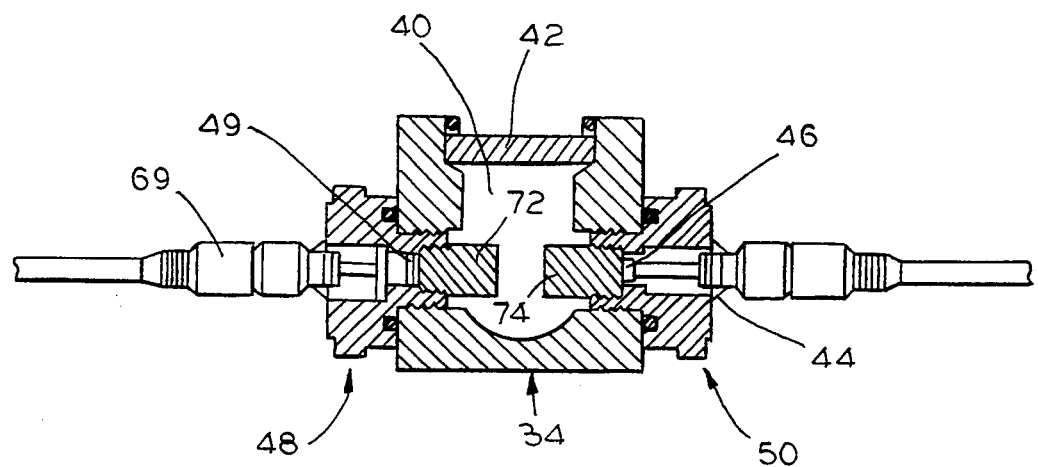
FIG. 2 is a cross sectional view of the inventive sensor in connection with a sample chamber.

In operation, the polymer solution passes continuously through the housing of the sensor chamber 36 (FIG. 2). The laser light source 49, operating in this example at a wavelength of 670 nm, is positioned inside the housing of sensor chamber 34 and behind a suitable lens assembly 72 located on one side of the monitored solution stream. The light passes from the laser source through the lens 72 and then through the polymer solution. After passing through the polymer solution, it enters a second lens assembly 74 on the opposite side of the solution stream. Located inside and behind the second lens assembly is a light selective filter (approximately 670 nm) and a CdS photoresistor 46.

The frequency which is selected for the laser depends on the type of polymer that is being monitored. Most synthetic polyelectrolytes, such as dispersions, emulsions, and natural polymers (corn starches, for example) respond well at the 670 nm wavelength. Solution polymers work best at or near infra-red wavelengths. However, for the entire range from visible light through infrared, all frequencies can be used to take advantage of unique molecular footprints and equivalent weights.

In this particular example, at 670 nm frequency, the signal appears to be linear, within 2% on a terminal point accuracy basis, and somewhat better than 1% on a best fit straight line basis.

The light intensity which is received at the resistor lens assembly 74 (FIG. 2) passes through a light selective filter prior to entering the CdS cell 46. By matching the light selective filter with the laser frequency, ambient light entering the sample chamber 34 through the viewing window 42 does not have a disruptive effect on the reading from CdS cell 46. Any small percent of the ambient light that has wavelengths that pass through the light selective filter are considered background noise which may be calibrated out of the reading, under almost all conditions.

The intensity of the light which is received at the resistor lens assembly 74 varies inversely with the concentration of the polymer solution.

The resistance of the CdS cell 46 is inversely variable with the intensity of the light. Due to these two inverse relationships acting in conjunction with each other, the output resistance becomes directly proportional to the concentration of the polymer solution.

The resistance of the CdS cell 46 is measured and converted into a process signal at resistance transmitter 68. This signal becomes the input signal to the electronic PID controller 70 (FIG. 4). A setpoint is entered into this controller 70 in order to vary its output signal in response to the measured input.

The controller 70 output signal is a control signal for adjusting the processing system of FIG. 1. Since it has been assumed for descriptive purposes that the controlled device 32 (FIG. 1) is a variable speed drive in FIG. 1, the usable output signal varies the speed of a positive displacement polymer injection pump. As the concentration of the polymer solution tends to decrease (i.e., water flow increases), neat polymer solids decrease, etc., the controller 70 (FIG. 4) increases its output signal, thus increasing the speed of a positive displacement pump. This causes more polymer to be metered to the polymer processing unit, thus increasing the concentration of the polymer solution. The usable output signal may cause the percent of polymer concentrate and active polymer solids to be displayed at 76. Another example would incorporate the use of a water flow control valve at a location where the polymer injection pump stays constant and the water flow is adjusted for concentration control.

For better performance, there are instances where the module for automatically controlling the polymer system can be tuned to operate below the threshold value of the laser. This is particularly true for polymer solutions with lower densities. In this case, the laser acts as a light emitting diode of a monochromatic nature with marginal coherency at a much lower energy level. In the inventive system, the laser driver can be adjusted to operate below the threshold current in order to accommodate such an application. This is useful when applying the unit to a broad range of applications. The flexibility inherent in this feature provides a means for processing different solutions of different concentrations, within the capability of the module for automatically controlling a polymer system.

One such application involves the use of the module for automatically controlling a system in the dairy industry. The module can be used as a standard component for evaluating the butter fat content in milk where the dairy industry typically back blends butter fat into milk. The module enables dairies to measure and adjust the milk/butter fat ratios to determine whether the milk is skim; <1%, low fat; 1-2%, whole 3-4%, etc. When used in a feedback loop, the module interfaces with a dairy central process computer in order to control and adjust butter fat content on a continuous production basis.

Those who are skilled in the art will readily perceive how to modify the invention. Therefore, the appended claims are to be construed to cover all equivalent structures which fall within the true scope and spirit of the invention.

The claimed invention is:

1. An automatic controller in combination with a polymer processing and delivery system for continuously controlling production of a polymer solution in said operating polymer processing and delivery system, said controller comprising optical analyzer means using coherent light for continuously monitoring concentration of polymer solids and controlling a polymer solids/hydrocarbon concentration of a polymer solution product at least while the system is in operation, said analyzer means including a sample chamber coupled to continuously receive and at all times contain an instantaneous aqueous sample of said polymer solution product, means for emitting said coherent light with a controlled amplitude and frequency into said sample, said light energy being scattered and absorbed by the polymer material dispersed throughout the instantaneous aqueous sample within the sample chamber, optical receiver means for measuring an amount of said coherent light energy received after said light passes through said instantaneous sample, said optical receiver means being adjustably located opposite the light emitting means, and means for converting an output from said receiver means into a usable process control signal for controlling said polymer system in order to maintain a high viscosity in said liquid.

2. The automatic controller means of claim 1 and means responsive to said usable process signal for displaying a readout in term of at least a percent of polymer concentration and active polymer solids.

3. The automatic controller means of claim 2 and feedback control loop means for providing a feedback signal for adjusting a polyelectrolyte in said concentration, and means responsive to said feedback signal in said feedback control loop means for controlling the polymer processing and delivery system.

4. The automatic controller means of claim 1 wherein said coherent light energy is selected from a range extending from visible through infrared light.

5. The automatic controller means of claim 1 wherein said polymer is taken from a group consisting of an emulsification, blended, activated, gels and processed polymer states.

6. The automatic controller means of claim 1 wherein said polymer is a dairy product.

7. The automatic controller of claim 1 wherein the coupling of said sample chamber is taken from a group consisting of a coupling for giving a partial flow, a bypass flow, a full flow, and a cascaded flow of said polymer solution product.

8. The automatic controller of claim 1 wherein said continuous flow of said polymer solution product flows in a range taken from the group consisting of 1-10 ft/sec or 0/0.3-25.0 ft/sec.

9. The automatic controller of claim 1 wherein said means for emitting and means for receiving said coherent light are set at a mutual angle in the range of 0°-60°.

10. The automatic controller of claim 1 and power supply means for delivering power to and for shutting down said power to said means for emitting coherent light responsive to an occurrence of a destructive voltage spike.

11. The controller of claim 10 and means for protecting a light diode if said diode is incorrectly connected or disconnected with a power supply which may generate voltage spikes.

12. The controller of claim 1 and fiber optical cables for connecting said means for emitting and receiving coherent light in order to locate said means away from a hot sample chamber.

13. The controller of claim 1 wherein said means for emitting said coherent light emits light taken from a group consisting of coherent laser light, monochromatic light, or a light with marginal coherency.

14. The controller of claim 1 wherein said means for emitting said coherent light emits light in the range of 660-680 mm a group consisting of coherent laser light, monochromatic light, or a light with marginal coherency.

15. The controller of claim 1 wherein said means for receiving coherent light is taken from a group consisting of a cadmium sulfide photoresistor and a photosilicon diode.

16. The controller of claim 1 wherein said means for emitting coherent light emits light at a frequency in a range extending from visible through infrared.

17. A polymer processing system controller in combination with a polymer processing system comprising means for continuously transporting a flowing solution stream through a sample chamber, means for directing a laser light beam through said solution while in said sample chamber whereby said continuously flowing solution stream has an effect upon said light, means for reading the light after said solution has had its effect upon the light, and means responsive to said reading means for adjusting said processing system to bring said read light into a predetermined state whereby a continuous manufacturing process may be automatically monitored.

18. The polymer controller of claim 17 and means for directing said laser light beam means and said means for reading said light at a mutual angle in the range of 0°-60°.

19. The polymer controller of claim 17 and means for connecting said transporting means into said processing system for continuously monitoring said solution, a mode of making said connection being taken from a group consisting of by-pass, partial or full stream monitoring.

20. A polymer processing system controller in combination with a polymer processing system comprising means for transporting a solution through a sample chamber, means for directing a laser light beam through said solution while in said sample chamber whereby said solution has an effect upon said light, means for reading the light after said solution has had its effect upon the light, and means responsive to said reading means for adjusting said processing system to bring said read light into a predetermined state, wherein said polymer processing system is a batch processing system and said means for connecting said transport means is coupled to measure said solution on a batch-by-batch basis.

* * * * *

UNITED STATES PATENT AND TRADEMARK OFFICE
CERTIFICATE OF CORRECTION

PATENT NO. : 5,403,552
DATED : April 4, 1995
INVENTOR(S) : Pardikes

It is certified that error appears in the above-indentified patent and that said Letters Patent is hereby corrected as shown below:

On the title page: Item

--[63] Continuation-in-part of Ser. No. 843,409, Feb. 28, 1992, abandoned, Ser. No. 871,066, Jun. 5, 1986, abandoned, Ser. No. 139,075, Dec. 28, 1987, abandoned, Ser. No. 352,689, May 10, 1989, abandoned, and Ser. No. 540,910, Jun. 20, 1990, abandoned.--

Column 1, line 11, delete "07/504,910" and insert -- 07/540,910--.

Column 1, lines 11-12, delete "now U.S. Pat. No.5,051,940" and insert --abandoned --.

Signed and Sealed this

Thirteenth Day of February, 1996

Attest:

BRUCE LEHMAN

Attesting Officer    Commissioner of Patents and Trademarks